(12) United States Patent
Roeper et al.

(10) Patent No.: US 8,273,896 B2
(45) Date of Patent: Sep. 25, 2012

(54) PROCESSES FOR PRODUCING PHENYL-6-(1-(PHENYL)UREIDO) NICOTINAMIDES

(75) Inventors: Stefanie Roeper, Cambridge, MA (US); Adam R. Looker, Cambridge, MA (US); Theodore A. Martinot, Jamaica Plain, MA (US); Bobbianna Neubert-Langille, Sudbury, MA (US); Michael P. Ryan, Roxbury, MA (US); John R. Snoonian, Bolton, MA (US)

(73) Assignee: Vertex Pharmaceutical Incorporated, Cambridge, MA (US)

( * ) Notice: Subject to any disclaimer, the term of this patent is extended or adjusted under 35 U.S.C. 154(b) by 339 days.

(21) Appl. No.: 12/704,903

(22) Filed: Feb. 12, 2010

(65) Prior Publication Data

US 2010/0234606 A1 Sep. 16, 2010

Related U.S. Application Data

(60) Provisional application No. 61/152,653, filed on Feb. 13, 2009.

(51) Int. Cl.
*C07D 213/36* (2006.01)
*C07D 213/78* (2006.01)

(52) U.S. Cl. ........................ 546/309; 546/310

(58) Field of Classification Search .................. None
See application file for complete search history.

(56) References Cited

U.S. PATENT DOCUMENTS 7,115,746 B2 * 10/2006 Snoonian et al. ............. 546/312

FOREIGN PATENT DOCUMENTS

WO WO2004/072038 8/2004

OTHER PUBLICATIONS

Caira, M.R., et al., "Crystalline Polymorphism of Organic Compounds", Topics in Current Chemistry, Springer, Berlin, vol. 198, 1998, pp. 163-208.
Stoica, C., et al., "Epitaxial 2D Nucleation of Stable Polymorphic Form of the Steroid 7alphaMNa", Int. Journal of Pharmaceutics, vol. 309, 2006, pp. 16-24.
International Search Report for PCT/US2010/024054, dated Oct. 26, 2010.

* cited by examiner

*Primary Examiner* — Yong Chu
(74) *Attorney, Agent, or Firm* — Honigman Miller Schwartz and Cohn LLP; Christopher C. Forbes; Jonathan P. O'Brien

(57) ABSTRACT

The present invention relates to processes for the preparation of compounds useful as inhibitors of p38 kinase. The processes of the present invention are amenable for large scale preparation and produce stable phenyl-6-(1-(phenyl)ureido) nicotinamides in high purity and yields.

6 Claims, No Drawings

PROCESSES FOR PRODUCING PHENYL-6-(1-(PHENYL)UREIDO) NICOTINAMIDES

CROSS-REFERENCE TO RELATED APPLICATIONS

This application claims priority to U.S. provisional application Ser. No. 61/152,653, which was filed on Feb. 13, 2009. The entire contents of U.S. provisional application Ser. No. 61/152,653 are incorporated herein in their entirety.

TECHNICAL FIELD OF THE INVENTION

The present invention relates to processes for the preparation of compounds useful as inhibitors of p38 kinase. The processes of the present invention are amenable for large scale preparation and produce stable phenyl-6-(1-(phenyl) ureido)nicotinamides in high purity and yields.

BACKGROUND OF THE INVENTION

Protein kinases are involved in various cellular responses to extracellular signals. Recently, a family of mitogen-activated protein kinases (MAPK) has been discovered. Members of this family are Ser/Thr kinases that activate their substrates by phosphorylation [B. Stein et al., Ann. Rep. Med. Chem., 31, pp. 289-98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor, CD14, and induced with LPS. p38 has since been isolated and sequenced, as has the cDNA encoding it in humans and mice. Activation of p38 has been observed in cells stimulated by stress, such as treatment of lipopolysaccharides (LPS), UV, anisomycin, or osmotic shock, and by cytokines, such as IL-1 and TNF.

Inhibition of p38 kinase leads to a blockade on the production of both IL-1 beta and TNF alpha. IL-1 and TNF stimulate the production of other proinflammatory cytokines such as IL-6 and IL-8 and have been implicated in acute and chronic inflammatory diseases and in post-menopausal osteoporosis [R. B. Kimble et al., Endocrinol., 136, pp. 3054-61 (1995)].

Based upon this finding, it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune disease, cell death, allergies, asthma, osteoporosis and neurodegenerative diseases. Inhibitors of p38 have also been implicated in the area of pain management through inhibition of prostaglandin endoperoxide synthase-2 induction. Other disease associated with IL-1, IL-6, IL-8 or TNF over-production are set forth in WO 96/21654.

2-(2,4-difluorophenyl)-6-(1-(2,6 difluorophenyl)ureido) nicotinamide (Compound I) having the structure depicted below, has demonstrated efficacy for the treatment of a variety of diseases, including acute and chronic inflammatory diseases. Compound I is described in WO 2004/72038, published on Aug. 26, 2004.

SUMMARY OF THE INVENTION

As described herein, the present invention provides processes for preparing p38 kinase inhibitors useful in the treatment of a number of diseases, including acute and chronic inflammatory diseases. Such compounds include 2-(2,4-difluorophenyl)-6-(1-(2,6 difluorophenyl)ureido)nicotinamide (Formula I) having the structure depicted below.

The processes of this invention have the advantage of allowing preparation of stable compounds of Formula 1 in high yield and purity, wherein $R_1$, $R_2$, $R_3$, $R_4$ and $R_5$ are defined below. The present invention has the additional advantage of facile reaction conditions that are readily scaled up for large scale preparation. Additionally, the processes provides a more rapid production of the desired products relative to prior routes by reducing reaction times needed to complete individual transformations, and by eliminating the need for additional purification steps.

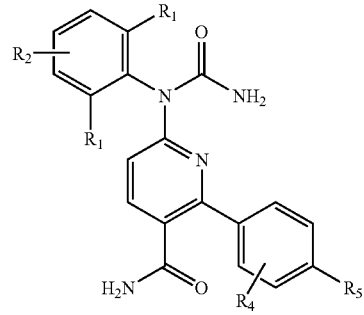

Formula 1

DETAILED DESCRIPTION OF THE INVENTION

Detailed Description of the Embodiments

In one aspect, this invention related to a process for preparing a compound of the Formula 4

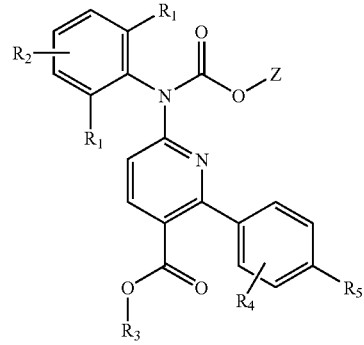

Formula 4 comprising coupling a compound of Formula 2

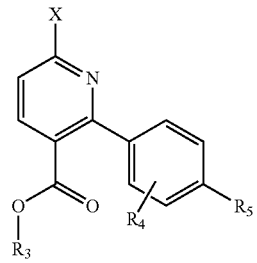

Formula 2 with a compound of Formula 3

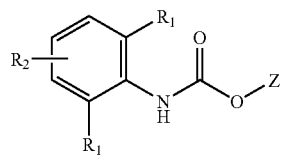

Formula 3 in the presence of a polar aprotic solvent.

Each $R_1$, $R_2$, $R_4$ and $R_5$ is independently selected from hydrogen, aliphatic, optionally substituted aryl, nitro, CN, OR', $CO_2R'$, $CO_2N(R')_2$, $NR'CO_2R'$, $NR'C(O)NR'_2$, $OC(O)NR'_2$, F, Cl, Br, I, OTs, OMs, $OSO_2R'$, OC(O)R'.

Each R' is independently selected from hydrogen, $C_{1-6}$ aliphatic, or a 5-6 membered carbocyclic or heterocyclic ring system optionally substituted with 1 to 3 substituents independently selected from halo, $C_{1-6}$ alkoxy, cyano, nitro, amino, hydroxy, and $C_{1-6}$ aliphatic.

Each $R_3$ is selected from hydrogen, $C_{1-6}$ aliphatic and aryl optionally substituted with $C_{1-6}$ aliphatic, aryl, nitro, CN, $CO_2R'$, $CO_2N(R')_2$, OR', $NCO_2R'$, $NR'C(O)N(R')_2$, or $OC(O)N(R')_2$.

Each X is independently a leaving group.

Each Z is independently selected from $C_{1-6}$ aliphatic, benzyl, Fmoc, or $-SO_2R'$.

In one embodiment of this aspect, the solvent is dimethyl sulfoxide (DMSO), N-Methylpyrrolidone (NMP), $CH_3CN$ or dimethylformamide (DMF).

In another embodiment, the solvent is DMSO.

In one embodiment of this aspect, the coupling of a compound of Formula 2 with a compound of Formula 3 is performed in the presence of a base.

In one embodiment of this aspect, the base is a metal carbonate or a metal phosphate.

In certain embodiments, the base is a metal carbonate, such as cesium carbonate or potassium carbonate.

In some specific embodiments, the base is cesium carbonate.

In other embodiments, the base is a metal phosphate, such as potassium phosphate.

In one embodiment of this aspect, the coupling of a compound of Formula 2 with a compound of Formula 3 is performed at a temperature range of about 55-75° C. In other embodiments of this aspect, the coupling of a compound of Formula 2 with a compound of Formula 3 is performed at a temperature range of about 50-65° C. In still further embodiments of this aspect, the coupling of a compound of Formula 2 with a compound of Formula 3 is performed at a temperature range of about 55-60° C.

In another aspect, this invention provides a process for preparing a compound of the Formula 5 comprising performing a hydrolysis on a compound of Formula 4

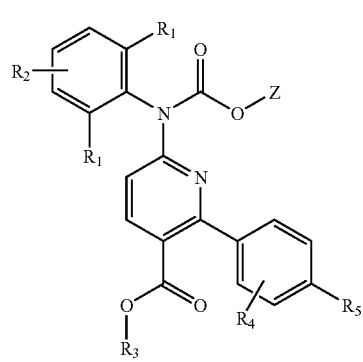

Formula 4 using a protic acid, wherein $R_1$, $R_2$, $R_4$, $R_5$, R', $R_3$ and Z are defined above.

In one embodiment of this aspect, the hydrolysis of a compound of Formula 4 is performed in the presence of a solvent.

In one embodiment of this aspect, the solvent is water.

In one embodiment of this aspect, the protic acid is sulfuric acid, HCl or $H_3PO_4$.

In certain embodiments, the protic acid is sulfuric acid.

In one embodiment of this aspect, the final concentration of sulfuric acid is about 7M.

In one embodiment of this aspect, the hydrolysis of a compound of Formula 4 is performed at a temperature range of about 60-105° C.

In certain embodiments, the hydrolysis of a compound of Formula 4 is performed at a temperature range of about 95-105° C.

In specific aspects, the hydrolysis of a compound of Formula 4 is performed at a temperature of about 100° C.

In one embodiment of this aspect, the hydrolysis of a compound of Formula 4 is performed using a one-pot reaction.

In another aspect, this invention provides a process for preparing a compound of the Formula 5

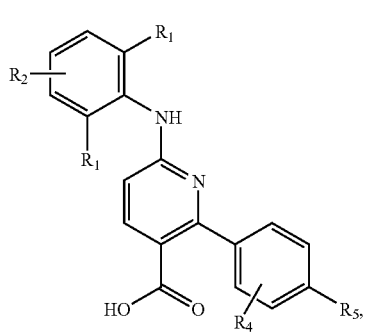

Formula 5

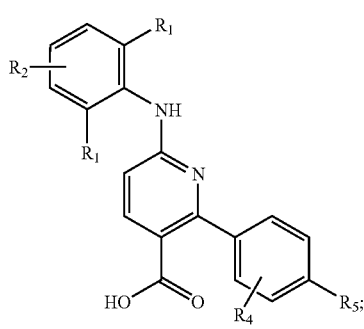

Formula 5 comprising performing a hydrolysis on a compound of Formula 2

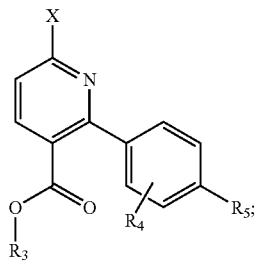

Formula 2 to provide a compound of Formula 12

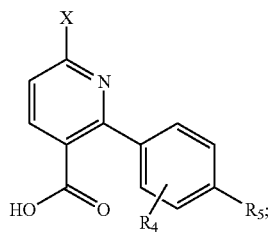

Formula 12 and coupling a compound of Formula 12 with a compound of Formula 11

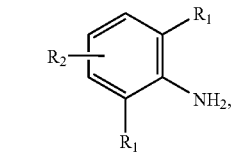

Formula 11 wherein $R_1$, $R_2$, $R_4$, $R_5$, R', $R_3$ and X are defined above.

In some embodiments of this aspect, the coupling is performed in the presence of a solvent.

In some further embodiments, the solvent can be selected from MTBE, THF, DMSO, MeTHF, Toluene, pyridine, DMF, dichloromethane, diethyl ether and ethyl acetate.

In some embodiments of this aspect, the coupling is performed in the presence of a base.

In other embodiments the base used in the coupling step can be selected from LiHMDS, NaHMDS, KHMDS, KOtBu, and nBuLi.

In some embodiments the base used in the coupling step is KHMDS.

In some embodiments the coupling reaction is performed at a temperature in the range of about −20° C. and 25° C. (for example, −20° C. to −10° C., −10° C. to −8° C., −10° C. to 0° C. or 0° C. to 25° C.).

In another aspect, this invention provides a process for preparing a compound of Formula 1

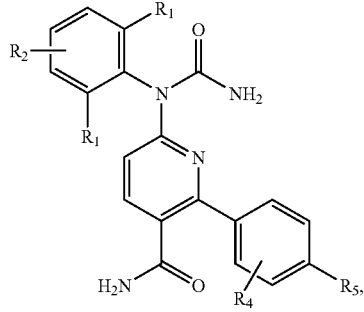

Formula 1 comprising performing an amidation and a urea formation on a compound of Formula 5

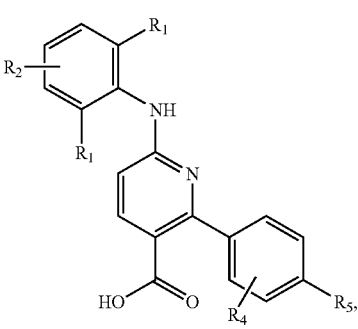

Formula 5 by treating a compound of Formula 5 with:
  i) a urea forming reagent;
  ii) an amidation reagent; and
  iii) anhydrous ammonia,
wherein
  each $R_1$, $R_2$, $R_4$ and $R_5$ is independently selected from hydrogen, aliphatic, optionally substituted aryl, nitro, CN, OR', $CO_2R'$, $CO_2N(R')_2$, $NR'CO_2R'$, NR'C(O)NR'$_2$, OC(O)NR'$_2$, F, Cl, Br, I, OTs, OMs, $OSO_2R'$, OC(O)R'; and
  each R' is independently selected from hydrogen, $C_{1-6}$ aliphatic, or a 5-6 membered carbocyclic or heterocyclic ring system optionally substituted with 1 to 3 substituents independently selected from halo, $C_{1-6}$ alkoxy, cyano, nitro, amino, hydroxy, and $C_{1-6}$ aliphatic.

In one embodiment of this aspect, the amidation reagent is phosgene, triphosgene or diphosgene.

In one embodiment of this aspect, the urea formation reagent is phosgene, triphosgene or diphosgene.

In one embodiment of this aspect, the amidation reagent and urea formation reagent are added at the same time.

In one embodiment of this aspect, the amidation reagent and urea formation reagent are the same.

In one embodiment of this aspect, the amidation and urea formation performed on a compound of Formula 5 are performed in the presence of a base.

In one embodiment of this aspect, the base is diisopropylethylamine, Huenigs base, or triethylamine.

In certain embodiments, the base is diisopropylethylamine.

In one embodiment of this aspect, the amidation and urea formation performed on a compound of Formula 5 are performed in the presence of a solvent.

In one embodiment of this aspect, the solvent is THF, MeTHF, or toluene.

In certain embodiments, the solvent is THF.

In one embodiment of this aspect, the compound of Formula 5 is treated with anhydrous ammonia after treatment with the amidation/urea formation reagent.

In one embodiment of this aspect, anhydrous ammonia is added to the product obtained after treatment of a compound of Formula 5 with the amidation/urea formation reagent, without isolation of said product.

In one embodiment of this aspect, the process further comprises isolating solid material after treating the solution with anhydrous ammonia, and washing the solid material with water followed by an acid wash to provide a compound of Formula 1.

In certain embodiments, the acid wash comprises a 1N $H_2SO_4$ wash of the solid material.

In another aspect, this invention provides a process of providing a stable solid form of a compound of Formula 1, comprising slurrying a solid form of a compound of Formula 1

Formula 1 wherein
each $R_1$, $R_2$, $R_4$ and $R_5$ is independently selected from hydrogen, aliphatic, optionally substituted aryl, nitro, CN, OR', $CO_2R'$, $CO_2N(R')_2$, NR'$CO_2R'$, NR'C(O)NR'$_2$, OC(O)NR'$_2$, F, Cl, Br, I, OTs, OMs, $OSO_2R'$, OC(O)R'; and
each R' is independently selected from hydrogen, $C_{1-6}$ aliphatic, or a 5-6 membered carbocyclic or heterocyclic ring system optionally substituted with 1 to 3 substituents independently selected from halo, $C_{1-6}$ alkoxy, cyano, nitro, amino, hydroxy, and $C_{1-6}$ aliphatic.

In one embodiment of this aspect, the compound of Formula 1 is stirred in a homogeneous or non-homogeneous solvent system.

In one embodiment of this aspect, the solvent system comprises methanol and water.

In one embodiment of this aspect, the methanol:water ratio in the solvent system is about 1:3.

In one embodiment of this aspect, the methanol:water ratio in the solvent system is about 1:1.

In one embodiment of this aspect, the compound is stirred for at least about 20 hours (e.g. about 24 hours).

In one embodiment of this aspect, the compound is stirred in a solvent system with a methanol:water ratio of about 1:3 for at least about 20 hours (e.g. about 24 hours), and then stirred in a solvent system with a methanol:water ratio of about 1:1 for at least about 20 hours (e.g. about 24 hours).

In one embodiment of this invention, each $R_1$, $R_2$, $R_4$ and $R_5$ is independently selected from hydrogen, F, Cl, Br, I, OTs or OMs.

In a further embodiment, each $R_1$, $R_2$, $R_4$ and $R_5$ is independently selected from hydrogen or F.

In one embodiment of this invention, each $R_3$ is independently selected from hydrogen or $C_{1-6}$ aliphatic.

In a further embodiment, each $R_3$ is independently selected from hydrogen or ethyl.

In one embodiment of this invention, each Z is independently $C_{1-6}$ aliphatic.

In a further embodiment, each Z is independently tert-butyl.

In another aspect, this invention provides a process for preparing Compound 10

10 comprising coupling Compound 11

11 with Compound 6

6 by dissolving Compounds 11 and 6 in Methyl tert-butylether (MTBE), treating the mixture with a base and stirring the mixture at a temperature of about −8° C. to −10° C. to obtain Compound 9

9 treating Compound 9 with triphosgene and diisopropylethylamine in the presence of tetrahydrofuran; stirring the solution until the reaction is complete; and treating the solution with anhydrous ammonia.

In one embodiment of this aspect, the base is LiHMDS, NaHMDS, KHMDS, KOtBu, or nBuLi.

In a further embodiment, the base is KHMDS.

In a further embodiment, the reaction temperature is between about −20° C. and 25° C. (for example, −20° C. to −10° C., −10° C. to −8° C., −10° C. to 0° C. or 0° C. to 25° C.).

In one embodiment of this aspect, the process further comprises isolating solid material after treating the solution with anhydrous ammonia, and washing the solid material with water followed by an acid wash to provide Compound 10.

In certain embodiments, the acid wash comprises a 1N $H_2SO_4$ wash of the solid material.

In another embodiment, the reaction temperature is about 55° C. In a further aspect, this invention provides a process for preparing a compound of Formula 5

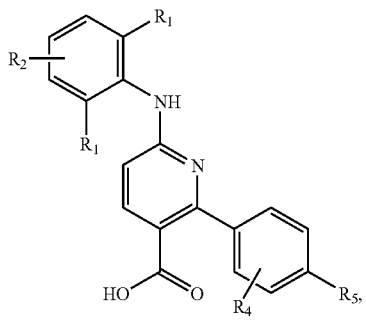

Formula 5 comprising performing a hydrolysis on a compound of Formula 7

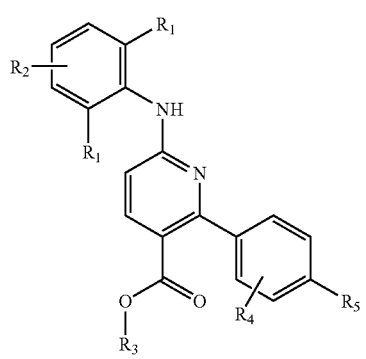

Formula 7 using a protic acid, wherein $R_1$, $R_2$, $R_4$, $R_5$, R' and $R_3$ are defined above.

In one embodiment of this aspect, the hydrolysis of Compound 11 is performed in the presence of a solvent.

In one embodiment of this aspect, the solvent is water.

In one embodiment of this aspect, the protic acid is sulfuric acid.

In one embodiment of this aspect, the final concentration of sulfuric acid is about 7M.

In another aspect, this invention provides a process for preparing Compound 10

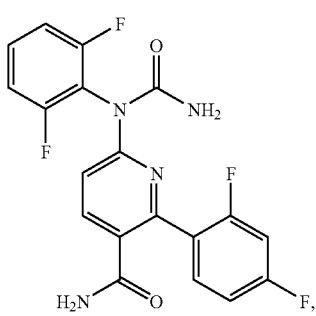

10 comprising coupling Compound 5

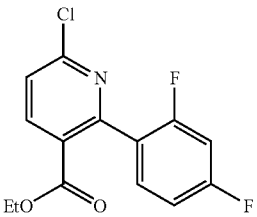

5 with Compound 7

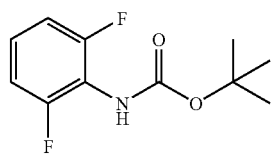

7 by dissolving Compounds 5 and 7 in dimethyl sulfoxide, treating the mixture with cesium carbonate and stirring the mixture at a temperature of about 50-65° C. (e.g. 55-60° C.) to obtain Compound 8

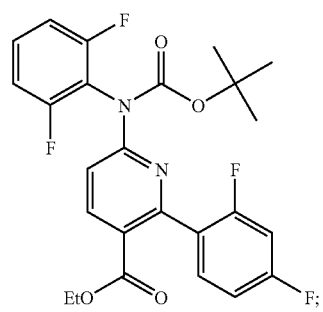

8 treating Compound 8 with an aqueous solution of about 7M sulfuric acid and stirring the mixture at a temperature of about 95-105° C. (e.g. 100° C.) to obtain Compound 9

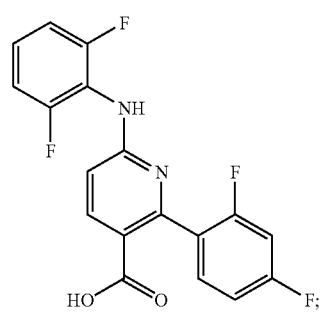

9 treating Compound 9 with triphosgene and diisopropylethylamine in the presence of tetrahydrofuran; stirring the solution until the reaction is complete; and treating the solution with anhydrous ammonia.

In one embodiment of this aspect, the process further comprises isolating solid material after treating the solution with anhydrous ammonia, and washing the solid material with water followed by an acid wash to provide Compound 10.

In certain embodiments, the acid wash comprises a 1N $H_2SO_4$ wash of the solid material.

In some further embodiments, the process comprises stirring Compound 10 in solvent system comprising methanol and water, wherein the methanol:water ratio is about 1:3 for at least about 20 hours (e.g. about 24 hours); adding methanol to the mixture to change the solvent ratio to about 1:1 methanol:water; and continuing stirring for at least about 20 hours (e.g. about 24 hours).

In one aspect, this invention includes a Compound produced by the process of any of the above embodiments.

In one aspect, this invention provides a pharmaceutical composition produced by the process of any of the above embodiments.

DEFINITIONS AND GENERAL TERMINOLOGY

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

As described herein, Compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic or tricyclic $C_8$-$C_{14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halo atoms. The term "halogen" or "halo" means F, Cl, Br, or I. Examples of haloaliphatic include —$CHF_2$, —$CH_2F$, —$CF_3$, —$CF_2$—, or perhaloalkyl, such as, —$CF_2CF_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined herein below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halo; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(O)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(O)N(R°)$_2$; —OC(O)N(R°)$_2$; —S(O)$_2$R°; —SO$_2$N(R°)$_2$; —S(O)R°; —NR°SO$_2$N(R°)$_2$; —NR°SO$_2$R°; —C(═S)N(R°)$_2$; —C(═NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halo, C$_{1-4}$aliphatic, OH, O(C$_{1-4}$aliphatic), NO$_2$, CN, CO$_2$H, CO$_2$(C$_{1-4}$aliphatic), O(halo C$_{1-4}$ aliphatic), or halo C$_{1-4}$aliphatic, wherein each of the foregoing C$_{1-4}$ aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHSO$_2$(alkyl), or ═NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$aliphatic)$_2$, halo, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$aliphatic), wherein each of the foregoing C$_{1-4}$ aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(═S)N(R$^+$)$_2$, —C(═NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH═CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R$^+$ are selected from NH$_2$, NH(C$_{1-4}$aliphatic), N(C$_{1-4}$ aliphatic)$_2$, halo, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R$^+$ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

The term "stable," as used herein, refers to compounds that are not substantially altered when subjected to conditions to allow for their production, detection, and preferably their recovery, purification, and use for one or more of the purposes disclosed herein, such as administration to a mammal by methods known in the art. In some embodiments, a stable compound or chemically feasible compound is one that is not substantially altered when kept at a temperature of 40° C. or less, in the absence of moisture or other chemically reactive conditions, for at least a week.

The term "leaving group," as used herein, has the definition described by "March's Advanced Organic Chemistry", 5$^{th}$ Ed., Ed.: Smith, M. B. and March, J., John Wiley & Sons, New York: 2001.

The term "amidation," as used herein, is defined as a process of producing an amide moiety. An example of a process of this type is, without limitation, the coupling of ammonia or an amine functionality with a compound bearing a carbonyl which itself bears a leaving group. A pictorial representation of a non-limiting, general example of the process of amidation, wherein X is a leaving group and R° is defined as above, is:

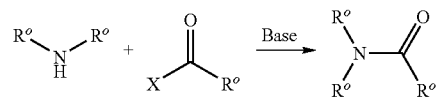

The term "urea" as used herein, is defined as any compound which contains in its structure a carbonyl bearing two amine functionalities. A pictorial representation of a non-limiting, general example of a urea, wherein R° is defined as above, is:

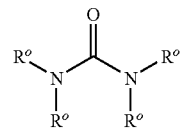

The term "urea forming reagent," as used herein, is defined as a carbonyl containing compound, wherein a carbonyl moiety bears two leaving groups, and can take part in the process of urea formation as defined below.

The term "urea formation," as used herein, is defined as a process of producing a urea moiety. An example of a process of this type is, without limitation, the coupling of ammonia or an amine functionality with a urea forming reagent. A pictorial representation of a non-limiting, general example of the process of urea formation, wherein $X_1$ and $X_2$ are leaving groups and $R^o$ is defined as above, is:

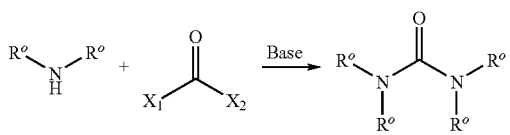

The term "one-pot reaction," as used herein, is defined as a process, wherein two or more distinct chemical transformations of a substrate occur upon the stepwise or simultaneous addition of one or more chemical reagents, without separation or purification of intermediate compounds.

The term "slurry," as used herein, is defined as a mixture comprising a solid and a liquid, wherein the solid is, at most, partially soluble in the liquid. The term "slurrying" or "slurried," as used herein (example, "the solid product was slurried for 24 hours"), is defined as the act of creating a slurry, and stirring said slurry for a length of time.

The term "protecting group," as used herein, represents those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups in Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenyl)-1)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are tert-butyloxycarbonyl (Boc).

Examples of useful protecting groups for acids are substituted alkyl esters such as 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropropylsysilylmethyl, cyanomethyl, acetol, phenacyl, substituted phenacyl esters, 2,2,2-trichloroethyl, 2-haloethyl, ω-chloroalkyl, 2-(trimethylsilyl)ethyl, 2-methylthioethyl, t-butyl, 3-methyl-3-pentyl, dicyclopropylmethyl, cyclopentyl, cyclohexyl, allyl, methallyl, cynnamyl, phenyl, silyl esters, benzyl and substituted benzyl esters, 2,6-dialkylphenyl esters such as pentafluorophenyl, 2,6-dialkylpyhenyl. Preferred protecting groups for acids are methyl or ethyl esters.

Methods of adding (a process generally referred to as "protection") and removing (process generally referred to as "deprotection") such amine and acid protecting groups are well-known in the art and available, for example in P. J. Kocienski, Protecting Groups, Thieme, 1994, which is hereby incorporated by reference in its entirety and in Greene and Wuts, *Protective Groups in Organic Synthesis*, 3$^{rd}$ Edition (John Wiley & Sons, New York, 1999).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or p. 38 inhibitors with improved therapeutic profile.

Processes and Intermediates

As used herein, abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

Compounds of Formula 1 can be synthesized according to Scheme 1.

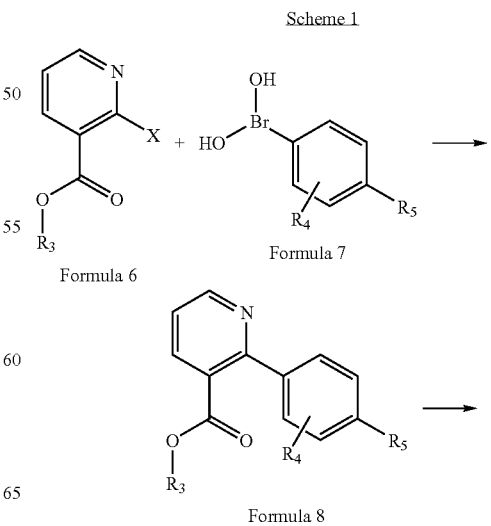

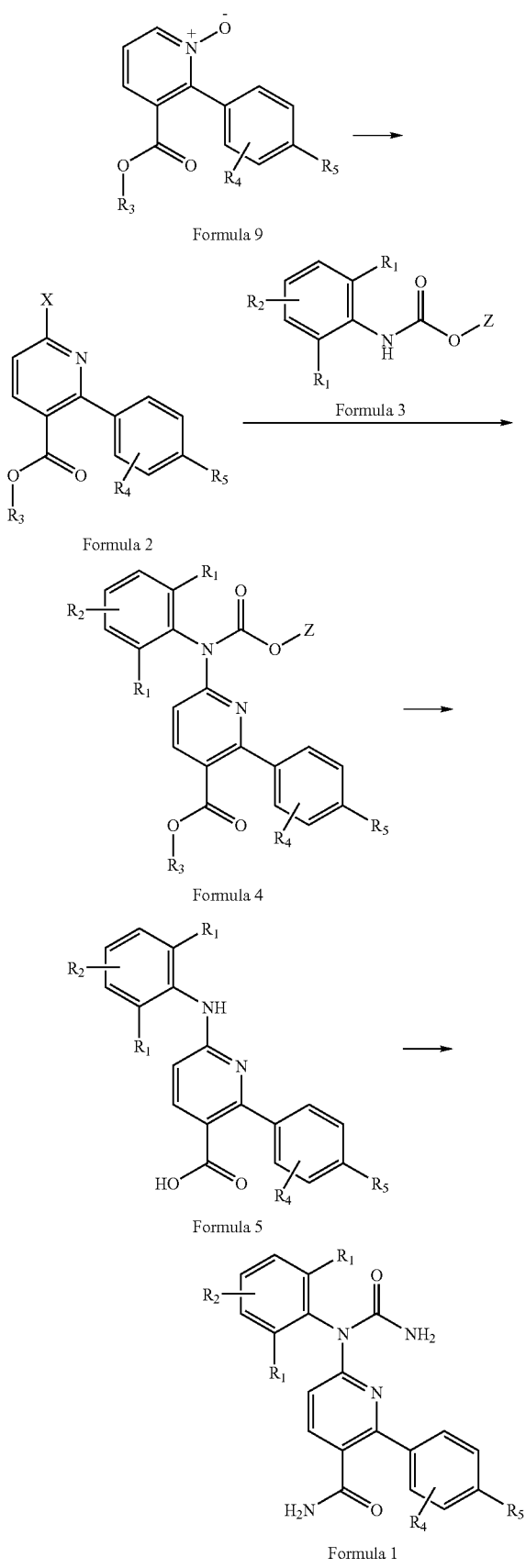

Compounds of Formula 8 can be prepared by coupling a compound of Formula 6, wherein X is a leaving group, with a boronic acid compound of Formula 7 in a suitable organic solvent (e.g. EtOH), in the presence of a suitable transition metal catalyst (e.g. Palladium tetrakis(triphenylphosphine)), in the presence of a suitable base (e.g. an alkali metal base such as $Na_2CO_3$) at temperatures between 70° C. and 90° C. Compounds of Formula 6 and 7 can be purchased commercially or synthesized using methods known to those skilled in the art.

An N-oxide compound of Formula 9 can be prepared from a compound of Formula 8 by oxidation with a suitable oxidizing agent (e.g. mCPBA) in a suitable solvent (e.g. $CH_2Cl_2$) at a suitable temperature (e.g. 20-40° C.).

A compound of Formula 2 can be synthesized by treatment of a compound of Formula 9 with a suitable agent such as a chlorinating agent (e.g. $POCl_3$), in a suitable solvent (e.g. 1,2-dichloroethane).

Compounds of Formula 4 can be synthesized by coupling a compound of Formula 2 with a compound of Formula 3 in the presence of a suitable alkali metal salt (e.g. cesium carbonate) and a suitable polar organic solvent (e.g. DMSO). Subsequently, the reaction mixture is treated with a suitable diluted aqueous acid (e.g. 1N HCl) and the product recrystallized from a suitable polar solvent (e.g. EtOH). Alternatively, compounds of Formula 4 can be prepared by coupling a compound of Formula 2 with a compound of Formula 3 in the presence of a transition metal catalyst (e.g. $Pd(OAc)_2$) as generally described in PCT application WO 2004/072038 and U.S. Pat. No. 7,115,746, the disclosures of which are hereby incorporated herein by reference in their entirety. Phenyl carbamates of Formula 4 can be purchased commercially or synthesized from the corresponding anilines using methods known to those skilled in the art.

Compounds of Formula 5 can be prepared from compounds of Formula 4 using a one-pot procedure wherein a compound of Formula 4 is treated with an acid in such a way to promote hydrolysis of the carbamate and ester functionalities. Alternatively, a compound of Formula 5 can be prepared from a compound of Formula 4 by first hydrolyzing the carbamate group followed by the hydrolysis of the ester to the corresponding carboxylic acid.

Compounds of Formula 1 can be prepared from compounds of Formula 5 by reacting a compound of Formula 5 with triphosgene or suitable equivalent reagent, followed by treatment with anhydrous ammonia.

Compounds of Formula 1 can also be recrystallized to a more stable form by treating a compound of Formula 1 with a mixture of water and a polar protic organic solvent.

EXAMPLES

The following preparative examples are set forth in order that this invention be more fully understood. These examples are for the purpose of illustration only and are not to be construed as limiting the scope of the invention in any way.

Example 1

Preparation of ethyl 6-chloro-2-(2,4-difluorophenyl)nicotinate (5)

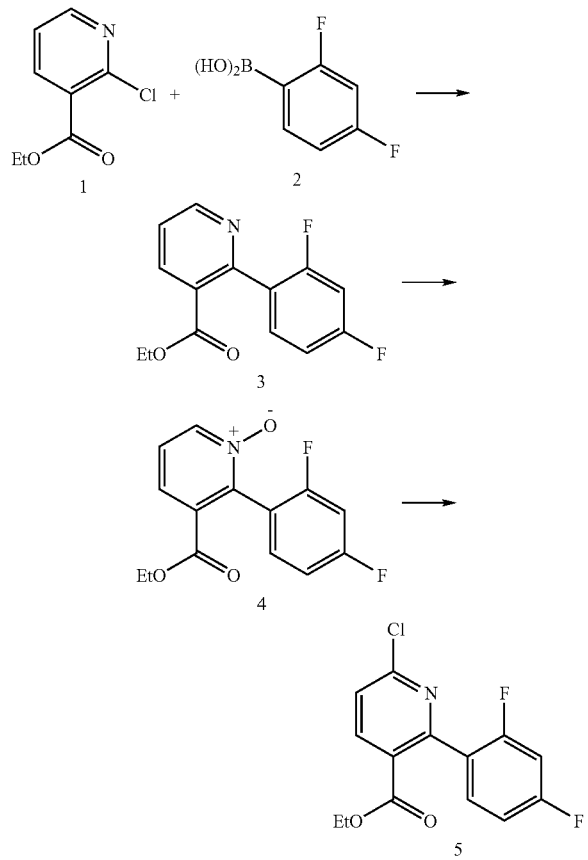

Preparation of ethyl 2-(2,4-difluorophenyl)nicotinate (3)

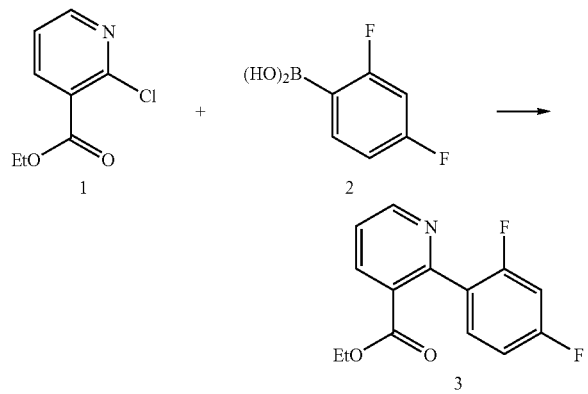

To a nitrogen purged 3.0 L, 4-necked flask, fitted with an overhead stirrer, thermocouple, heating mantle, nitrogen outlet and reflux condenser, was charged Pd(Ph$_3$)$_4$ (5.0 g, 4.33 mmoles, 0.005 eq), sodium carbonate (92.6 g, 874 mmoles, 1.3 eq), ethyl 2-chloronicotinate, 1 (126.0 g, 678 moles, 1.0 eq), 2,4-difluorophenylboronic acid, 2 (125 g, 791 mmoles, 1.2 eq), followed by 0.5 L of toluene and 125 mL denatured EtOH. The reaction was heated to 82° C. with vigorous stirring under N$_2$ overnight (completeness of reaction determined by HPLC and TLC). The reaction was cooled to room temperature, the mixture filtered through a small pad of Celite® and the solvents removed under vacuum at 55° C. The residue was dissolved in EtOAc, washed, dried (MgSO$_4$), filtered through Celite® again, and concentrated. The product was obtained as a yellow solid.

Preparation of 2-(2,4-difluorophenyl)-3-(ethoxycarbonyl)pyridine 1-oxide (4)

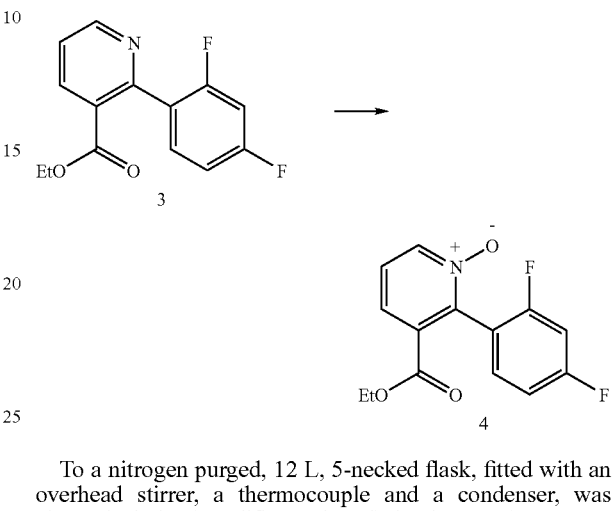

To a nitrogen purged, 12 L, 5-necked flask, fitted with an overhead stirrer, a thermocouple and a condenser, was charged ethyl 2-(2,4-difluorophenyl)nicotinate, 3 (144 g, 548 mmoles, 1.0 eq), and 4 L of CH$_2$Cl$_2$. With stirring, mCPBA was added over 5 minutes, and the temperature was gradually increased from 22 to 38° C. in 45 minutes (completeness of reaction determined by HPLC). The reaction was cooled to room temperature and the contents slowly poured into 3 L of water. Na$_2$SO$_3$ was added slowly (exotherm from 20 to 33° C.) until the peroxide test (starch/I$_2$ paper) indicated no peroxides remained in the mixture. The aqueous layer was separated and the organic layer was washed with saturated NaHCO$_3$ (~3 L). The organic layer was dried with MgSO$_4$, filtered, and concentrated to a brown thick oil. The oil was then treated with MTBE (2 L) and stirred to give a white precipitate, which was collected by filtration, washed with MTBE and dried under vacuum to give the title Compound 4.

Preparation of ethyl 6-chloro-2-(2,4-difluorophenyl)nicotinate (5)

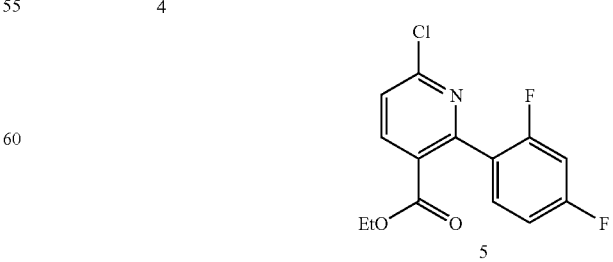

To a nitrogen purged 500 mL, 3-necked flask, fitted with a reflux condenser, heating mantle and a thermocouple was charged 2-(2,4-difluorophenyl)-3-(ethoxycarbonyl)pyridine 1-oxide, 4 (21 g, 75 mmoles, 1.0 eq), followed by 150 mL dichloroethane. Phosphorous oxychloride (75 mL) was added in one aliquate with stirring, causing an immediate rise in temperature from 21 to 23° C. followed by gradual warming. The solution was heated under nitrogen to 70-75° C. (completeness of reaction determined by HPLC). The reaction was then cooled to room temperature and concentrated under vacuum to remove most of the POCl₃. The remainder was quenched by slowly pouring onto 450 g of ice. The mixture (after the ice melted) was then extracted into methylene chloride (2×200 mL). The combined organics were dried (MgSO₄), filtered through silica, eluted with methylene chloride, and concentrated to give the title Compound, 5, as an orange solid. $^1$H NMR (500.0 MHz, CDCl₃) d 8.15 (d, J=8.2 Hz, 1H), 7.54 (td, J=8.5, 5.0 Hz, 1H), 7.34 (d, J=8.2 Hz, 1H), 6.96-6.92 (m, 1H), 6.79-6.74 (m, 1H), 4.16 (q, J=7.2 Hz, 2H), 1.10 (t, J=7.1 Hz, H) ppm.

Example 2

Preparation of tert-butyl 2,6-difluorophenylcarbamate (7)

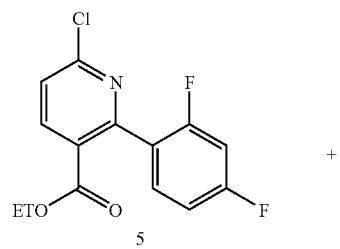

2,6-Difluoroaniline, 6 (4.5 mL, 42 mmol, 1.0 equiv.), and Boc anhydride (11.1 g, 51 mmol, 1.2 equiv.) were mixed in THF and to this mixture was added 1M sodium hexamethyldisilazide (100 mL, 100 mmol, 2.3 equiv.) at room temperature (completeness of reaction determined by HPLC). 50 mL brine was then added, and the solution was concentrated and extracted with EtOAc (2×100 mL). The combined organics were washed with brine (1×50 mL), followed by citric acid (2×10%). The resulting solution was then dried over MgSO₄, filtered and concentrated to give the title Compound, 7, as an orange solid which was used directly in the next step without additional purification. $^1$H NMR (500.0 MHz, CDCl₃) 7.18-7.13 (m, 1H), 6.96-6.91 (m, 2H), 6.06 (s, 1H) and 1.52 (s, 9H) ppm Example 3

Preparation of ethyl 6-(tert-butoxycarbonyl(2,6-difluorophenyl)amino)-2-(2,4-difluorophenyl)nicotinate (8)

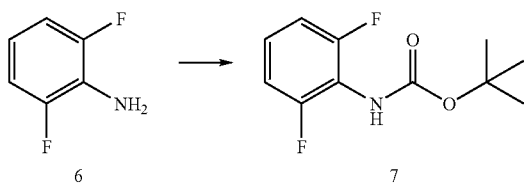

+

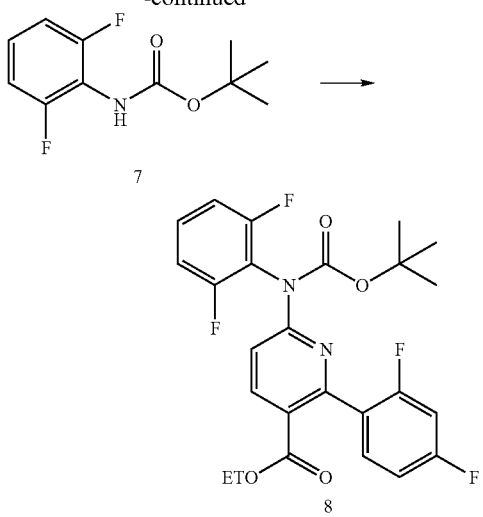

A mixture of Compound 5 (100.82 g, 0.33 mol, 1.0 equiv.), Compound 7 (101.05 g, 0.44 mol, 1.30 eq), and cesium carbonate (177.12 g, 0.54 mol, 1.60 eq) was suspended in DMSO (250 mL, 2.5 volumes) and stirred vigorously at 55-60° C. for 48 hours (completeness of reaction determined by HPLC). The mixture was cooled to 20-30° C. and the base was quenched by careful and slow addition of a 1 N HCl (aq) solution (540 mL, 1.60 eq), keeping the internal temperature of the reaction mixture below 30° C. Upon cooling, a precipitate formed and was filtered and washed with water (2×250 mL, 2×2.5 volumes). The precipitate was then suspended in absolute ethanol (1000 mL, 10 volumes) and heated to reflux. The reflux was maintained for 30-60 minutes, and water (200 mL, 2 volumes) was added to the mixture. The resulting mixture was then heated again to reflux, and reflux was maintained for 30 minutes, at which point the suspension was cooled to 10° C. The resulting solids were then filtered and washed with water (2×250 mL, 2×2.5 volumes), followed by absolute ethanol (250 mL, 2.5 volumes), and then transferred to a vacuum oven and dried at 50-60° C. The title Compound, 8, was obtained as a white crystalline solid. ($^1$H NMR, 500 MHz; CDCl₃) δ 8.28 (d, 1H), 8.12 (d, 1H), 7.19 (q, 1H), 6.96 (t, 2H), 6.81 (t, 1H), 6.74 (t, 1H), 4.25 (q, 2H), 1.50 (s, 9H), 1.20 (t, 3H).

Example 4

Preparation of 2-(2,4-difluorophenyl)-6-(2,6-difluorophenylamino)nicotinic acid (9)

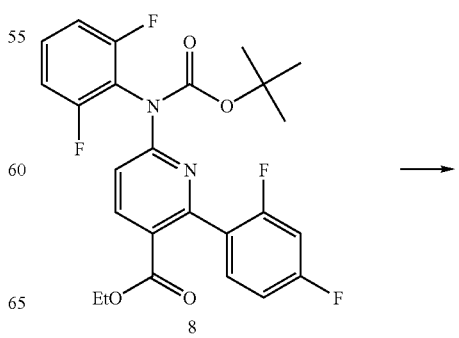

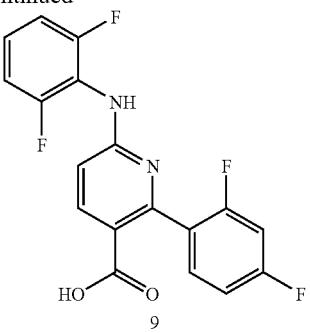

9

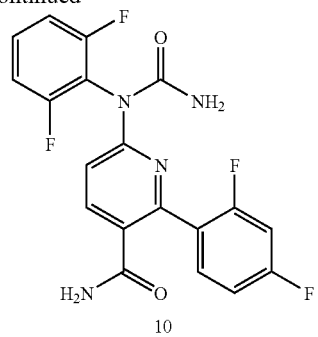

10

To Compound 8 (100 g, 0.204 mol, 1.00 eq) was added a 7M sulfuric acid solution prepared by the slow addition of concentrated sulfuric acid (285 mL, 2.85 vol, 5.24 mol) to distilled water (465 mL, 4.65 vol) while keeping the temperature below 50° C. The mixture was heated at 100±5° C. until the reaction was complete. The mixture was then cooled to 30±5° C. and additional water (750 mL, 7.5 vol) was added. Isopropyl acetate (2 L, 20 vol) was then added and the mixture was stirred for 15 minutes. Stirring was stopped and the phases were allowed to separate. The aqueous phase was separated and water (7.5 vol) was charged to the organic phase. The mixture was stirred for 15 minutes, polish filtered, then the aqueous phase was drained. The total volume of the organic layer was reduced to 4 vol by vacuum distillation at 45±5° C. The resulting slurry was cooled to −10° C. for 12 hours and filtered. The filter and cake was washed with cold isopropyl acetate (3 vol) and the solids were dried under vacuum at 50±5° C. to give the title Compound, 9, as a white solid. ($^1$H NMR, 500 MHz; DMSO-$d_6$) δ 12.50 (s, 1H), 9.25 (s, 1H), 8.07 (d, 1H), 7.39 (q, 1H), 7.29 (m, 1H), 7.18 (m, 3H), 7.09 (m, 1H), 6.25 (m, 1H).

Example 5

Preparation of 2-(2,4-difluorophenyl)-6-(1-(2,6-difluorophenyl)ureido)nicotinamide (10)

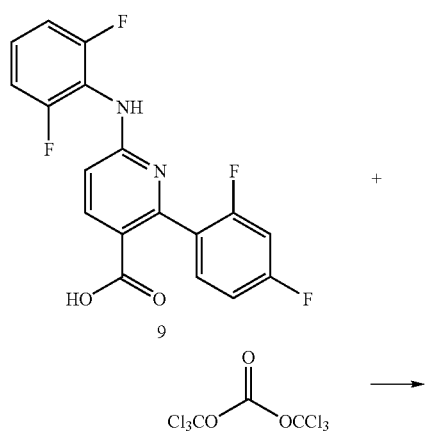

Triphosgene (38.87 g, 0.1276 mol, 0.9 eq) and Compound 9 (51.14 g, 0.1412 mo, 1 eq.) were charged to a reactor. Anhydrous THF (486 mL, 9.5 vol) was then added and the clear solution was cooled to −30±5° C. Diisopropylethylamine (73.79 mL, 0.424 mol, 3.0 eq) in THF (103 mL, 2.5 vol) was charged to the reactor keeping the temperature below −20° C. After addition, the reaction mixture was warmed to 20±3° C. The mixture was stirred for 2 hours and was then filtered through Celite®, and the cake was rinsed with THF (767 mL, 15 vol). The filtrate was cooled to −30° C. and anhydrous NH$_3$ (3 equiv.) added. The resulting white slurry was purged with N$_2$ and warmed up to 20±3° C. for 1 hour. The reaction mixture was then cooled to 0±5° C. for 30 minutes. The mixture was again filtered and the reactor was rinsed with THF (255 mL, 5 vol). The cake was rinsed with H$_2$O (255 mL, 5.0 vol) followed by 1N H$_2$SO$_4$ (10 vol). The solid was then transferred to a vacuum oven and dried at 35±3° C. to give the title Compound, 10, as a white solid. ($^1$H NMR, 500 MHz; DMSO-$d_6$) δ 7.97 (d, 1H), 7.85 (s, 1H), 7.56 (quin, 1H), 7.45 (q, 1H), 7.40 (s, 2H), 7.28 (t, 3H), 7.15 (td, 1H), 7.06 (d, 1H).

Example 6

Preparation of a solid form of 2-(2,4-difluorophenyl)-6-(1-(2,6-difluorophenyl)ureido)nicotinamide (10)

10

A slurry of Compound 10 (407.74 mL, 1.01 mol, 1.00 eq) in methanol (6.52 L, 16.0 vol) was heated to 60° C. until a solution was obtained. The reactor contents were then cooled to 48° C., held at this temperature until crystallization set in, stirred for 30 minutes and then cooled to 0° C. The slurry was filtered off, the reactor and filter cake were rinsed with methanol (816 mL, 2 vol) previously cooled to 0-5° C. The filter cake was dried under vacuum for 30 minutes. The solid was then returned to the reactor and stirred with a 1:3 methanol:

water mixture (4.1 L, 10 vol) at 22° C. for 24 hours. Methanol (2.05 L, 5 vol) was added to the reactor, resulting in a 1:1 methanol:water mixture. This solution was then stirred for an additional 24 hours, after which the mixture was filtered, and the cake was rinsed with water (818 L, 2 vol). The solids were transferred to a vacuum oven and dried at 38° C. to give Compound 10 as a white solid.

Example 7

Alternative Route to 2-(2,4-difluorophenyl-1)-6-(2,6-difluorophenylamino)nicotinic acid (9)

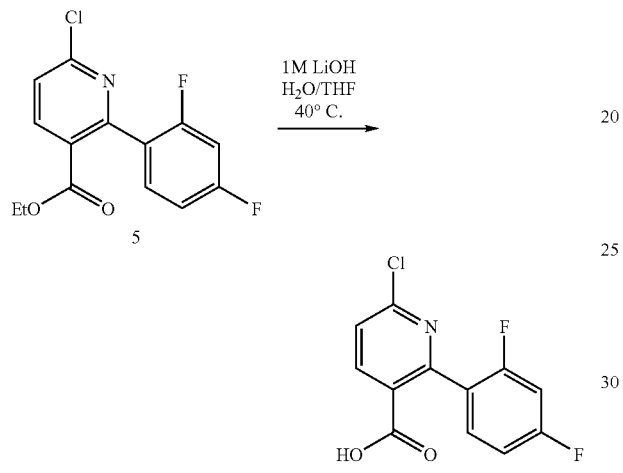

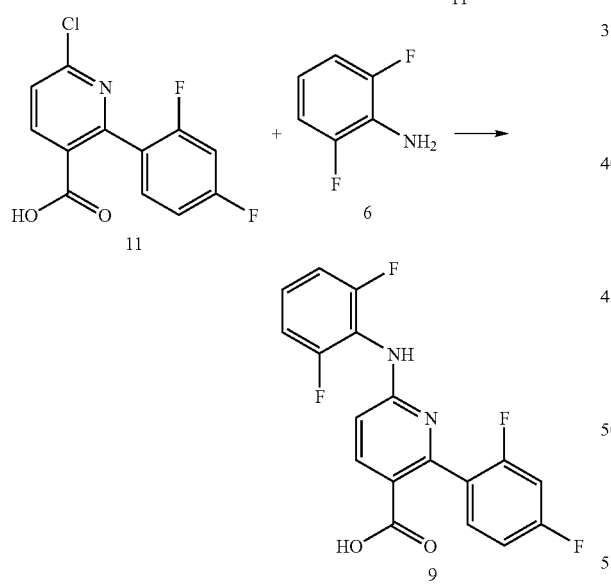

Step A: Saponification:

A 250 mL round bottom flask was charged with Compound 5 and THF at room temperature. A 1M LiOH solution was then added to flask. The resulting mixture was heated to approximately 40° C. for about 3 hours and then cooled down room temperature and stirred for about 2 days. The reaction can be monitored by HPLC. After stirring, the mixture was transferred to a separatory funnel, 100 mL DCM was added, and the mixture was washed with 100 mL water. The organic layer was separated and aqueous phase was neutralized with 110 mL aqueous 1N HCl and extracted with DCM (3×100 mL). The organic layers were combined and concentrated to provide Compound 11 as a white solid. H NMR (500.0 MHz, DMSO) 13.5 (bs, OH) d 8.31 (d, J=8.3 Hz, H), 7.70 (d, J=8.2 Hz, H), 7.62 (dd, J=8.6, 15.2 Hz, H), 7.35-7.31 (m, H), 7.21 (td, J=8.5, 3.6 Hz, H), 3.33 (s, H), 2.51 (d, J=1.7 Hz, H) ppm.

Step B: Coupling

A 100 mL round bottom flask was charged with Compound 20 (1.0015 g, 3.714 mmol) in MBTE (10 mL) followed by the addition of Compound 6 (600 µL, 5.572 mmol). The resulting mixture was cooled to an internal temperature of −8° C. to −10° C. with an ice/acetone bath followed by the dropwise addition (over 1 hour) of a 1 M solution of potassium bis(trimethylsilyl)amide (9.3 mL, 9.300 mmol) while maintaining the mixture temperature at less than about −5° C. After the addition of the base, the reaction mixture was quenched with 20 mL 1 M HCl at room temperature. The mixture was washed with 20 mL water and 50 mL ethyl acetate. The aqueous phase was washed at least once more with ethyl acetate. The organic layer was concentrated followed by the addition of DCM (25 mL). The resulting solids were suspended, filtered, and washed with 50 mL DCM. Analysis of the solids confirmed the presence of Compound 9.

In other embodiments the base used in the coupling step can also be selected from LiHMDS (55° C.), NaHMDS (55° C.), KOtBu, and nBuLi.

Example 8

Alternative Route to 2-(2,4-difluorophenyl)-6-(1-(2,6-difluorophenyl)ureido)nicotinamide (10)

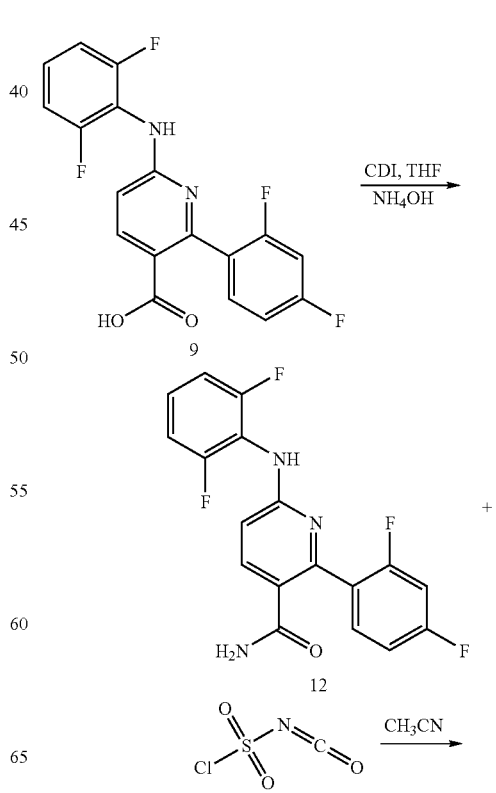

-continued

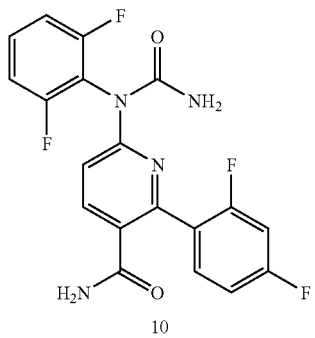
10

In some embodiments, Compound 10 can be produced by stepwise formation of amide Compound 12 using CDI, THF, NH₄OH or toluene/Methylchloroformate/NEt₃/NH₄OH. Compound 10 can be subsequently formed by treating Compound 15 with chlorosulfonylisocyanate in a solvent such as CH₃CN, DMSO, MeTHF, THF, DMF, or DMSO.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

We claim:
1. A process for preparing Compound 10

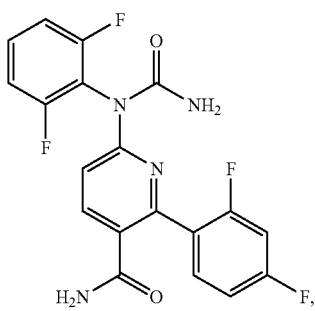
10 comprising coupling Compound 11

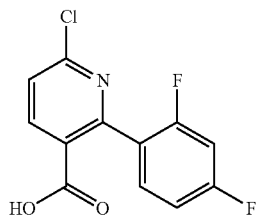
11 with Compound 6

6 by dissolving Compounds 11 and 6 in Methyl tert-butylether (MTBE), treating the mixture with a base and stirring the mixture at a temperature of about −8° C. to −10° C. to obtain Compound 9

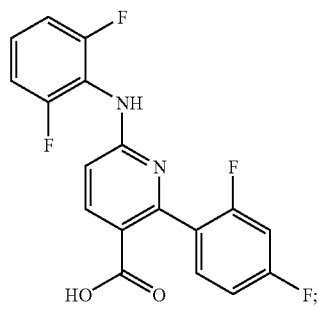
9 treating Compound 9 with triphosgene and diisopropylethylamine in the presence of tetrahydrofuran; stirring the solution; and treating the solution with anhydrous ammonia.

2. The process of claim 1, wherein the base is LiHMDS, NaHMDS, KHMDS, KOtBu, or nBuLi.

3. The process of claim 2, wherein the base is KHMDS.

4. The process of claim 1, further comprising isolating solid material after treating the solution with anhydrous ammonia, and washing the solid material with water followed by an acid wash to provide Compound 10.

5. The process of claim 4, wherein the acid wash comprises a 1N H₂SO₄ wash of the solid material.

6. The process of claim 1, further comprising stirring Compound 10 in solvent system comprising methanol and water, wherein the methanol:water ratio is about 1:3 for at least about 20 hours; adding methanol to the mixture to change the solvent ratio to about 1:1 methanol:water; and continuing stirring for at least about 20 hours.

* * * * *